(12) United States Patent
Nieschlag et al.

(10) Patent No.: US 7,025,979 B2
(45) Date of Patent: Apr. 11, 2006

(54) MALE CONTRACEPTIVE FORMULATION COMPRISING NORETHISTERONE

(75) Inventors: Eberhard Nieschlag, Muenster (DE); Axel Kamischke, Muenster (DE); Michael Oettel, Jena (DE); Alexander Ruebig, Berlin (DE); Ekkerhard Schillinger, Berlin (DE); Ursula-Friederike Habenicht, Berlin (DE)

(73) Assignee: Schering AG, Berlin (DE)

( * ) Notice: Subject to any disclaimer, the term of this patent is extended or adjusted under 35 U.S.C. 154(b) by 107 days.

(21) Appl. No.: 09/764,149

(22) Filed: Jan. 19, 2001

(65) Prior Publication Data

US 2002/0103176 A1  Aug. 1, 2002

Related U.S. Application Data

(60) Provisional application No. 60/266,326, filed on Feb. 15, 2000.

(51) Int. Cl.
*A61K 9/00* (2006.01)
*A61K 9/08* (2006.01)
*A61K 9/10* (2006.01)
*A61K 9/70* (2006.01)
*A61K 31/56* (2006.01)

(52) U.S. Cl. ............ 424/422; 424/400; 424/443; 514/170

(58) Field of Classification Search ......... 424/422, 424/434, 435, 443, 400; 514/170
See application file for complete search history.

(56) References Cited

U.S. PATENT DOCUMENTS

| | | | |
|---|---|---|---|
| 4,018,919 A | 4/1977 | Black | |
| 4,210,644 A | 7/1980 | Ewing et al. | |
| 5,035,891 A | 7/1991 | Runkel et al. | |
| 5,583,129 A * | 12/1996 | Spona et al. | 514/178 |
| 5,633,242 A | 5/1997 | Oettel et al. | |
| 5,711,962 A | 1/1998 | Cordes et al. | |
| 5,811,117 A | 9/1998 | Hashimoto et al. | |
| 5,855,905 A | 1/1999 | Oettel et al. | |
| RE36,247 E | 7/1999 | Plunkett et al. | |
| 5,965,552 A | 10/1999 | Berliner et al. | |

FOREIGN PATENT DOCUMENTS

| | | |
|---|---|---|
| DE | 27 14 240 A1 | 10/1977 |
| DE | 196 50 352 A1 | 7/1998 |
| EP | 0 773 028 A1 | 5/1997 |
| WO | WO 95/12383 A1 | 5/1995 |

OTHER PUBLICATIONS

Guerin et al., "Inhibition of spermatogenesis in men using various combinations of oral progestagens and percutaneous or oral androgens." International Journal of Andrology, vol. 11, pp. 187-199, 1988.*
E. Nieschlag et al., "Testosterone Therapy," *Male Reproductive Health and Dysfunction*, pp. 297-309 (1997).
Beatrize Couzinet et al., "The Antigonadotropic Activity of Progestins (19-Nortestosterone and 19-Norprogesterone Derivatives) Is not Mediated through the Androgen Recpetor," *Journal of Clinical Endocrinology and Metabolism*, 81, No. 12, pp. 4218-4223 (1996).
M.A. Okon et al., "A prospective randomized controlled study comparing the morphological and biochemical responses to the endometrium to two different forms of "period free" hormone replacement therapy," *Human Reproduction*, 31, No. 8, pp. 2261-2265 (1998).
J.F. Guerin et al., "Inhibition of spermatogenesis in men using various combinations of oral progestagens and percutaneous or oral androgens," *International Journal of Andrology*, 11, pp. 187-199 (1988).
M.C. Merrigiola et al., "Low Dose of Cyproterone acetate and testosterone enanthate for contraception in men" *Human Reproduction*, 13, pp. 1225-1229 (1998).
Eds. Nieschlag E. Behre HM, "Experimental Approaches," *Hormone Male Contraception Andrology—Male reproductive Health and Dysfunction*, pp. 388-393 (1997).
F. Neuman et al., "Androgens II and Anti-Androgens," *Springer-Verlag, Berlin, Heidelberg*, pp. 436-437 (1974).
Fuhrmann et al., "Stable transfection of androgen recpetor and MMTV-CAT into mammalian cells: inhibition of cat expression by anti-androgens," *J. Steroid Biochem. Mol. Biol.*, 42(8), p. 787 (1992).

(Continued)

*Primary Examiner*—Michael Hartley
*Assistant Examiner*—Simon J. Oh
(74) *Attorney, Agent, or Firm*—Millen, White, Zelano, Branigan, P.C.

(57) ABSTRACT

A formulation for male contraception comprising a progestin possessing both estrogenic and androgenic properties is remarkably effective for spermatogenesis suppression in males. The progestin Norethisterone (NET), particularly its derivatives Norethisterone acetate and Norethisterone enanthate in sufficient doses induce oligozoospermia or azoospermia in males. Formulations further comprising an androgen, such as a testosterone derivative such as a testosterone ester, particularly testosterone undecanoate, are especially effective male contraceptive formulations.

33 Claims, No Drawings

OTHER PUBLICATIONS

K.H. Fritzemeier et al., "In Vitro and In Vivo Models to Characterize Estrogens and Antiestrogens," *Handbook of Experimental Pharmacology*, vol. 135, pp. 6-43 (1999).

E. Nieschlag et al., "Testosterone in male contraception," *Testosterone: action, deficiency, substitution*, pp. 513-528 (1998).

H.M. Behre et al., "Potential of Testosterone Buciclate for Male Contraception: Endocrine Differences between Responders and Nonresponders," *Journal of Clinical Endocrinology and Metabolism*, 80, No. 8, pp. 2394-2403 (1995).

M.C. Merrigiola et al., "A combined regimen of cyproterone acetate and testosterone enanthate as a potentially highly effective male contraceptive," *Journal of Clinical Endocrinology and Metabolism*, 81, pp. 3018-3023 (1996).

R.A. Bebb, "Combined administration of levonorgestrel and testosterone induces more rapid and effective suppression of spermatogenesis than testosterone alone: a promising male contraceptive approach," *Journal of Clinical Endocrinology and Metabolism*, 81, pp. 757-762 (1996).

C.J. Bagatell et al., "Comparison of a Gonadotropin releasing-hormone antagonist plus testosterone (T) versus T alone as potential male contraceptive regimens," *Journal of Clinical Endocrinology and Metabolism*, 77, No. 2, pp. 427-432 (1997).

M.C. Merrigiola et al., "An oral regimen of cyproterone acetate and testosterone undecanoate for spermatogenic suppression in men," *Fertility and Sterility*, 68, pp. 84-850 (1997).

World Health Organization, "Contraceptive efficacy of testosterone-induced azoospermia and oligozoospermia in normal men," *Fertility and Sterility*, 65, pp. 84-850 (1997).

D. Buechter et al., "Clinical trial of transdermal testosterone and oral levonorgestrel for male contraception,"0 *The Journal of Clinical Endocrinology & Metabolism* 84, No. 4, pp. 1244-1249 (1999).

English Abstract of WO96/03131 dated Feb. 8, 1996.

World Health Organization, "Contraceptive efficacy of testosterone-induced azoospermia in normal men," *The Lancet*, 336, pp. 955-959 (1990).

Born et al., "Investigations upon the mechanism of inhibition of spermatogenesis in the rat by a dimeric ethynodiol-testosterone ester," *Acta Endocrinologica (Copenh)*, 1988, 117, pp. 536-544.

Sánchez et al., "Inhibition of Spermatogenesis with Monthly Injections of Medroxyprogesterone Acetate and Low Dose Testosterone Enanthate," *International Journal of Andrology*, 2(1979), pp. 136-149.

* cited by examiner

MALE CONTRACEPTIVE FORMULATION COMPRISING NORETHISTERONE

This application claims benefit of the filing date of provisional application filed Feb. 15, 2000 60/266,326, corresponding to converted non-provisional application Ser. No. 09/503,729.

FIELD OF INVENTION

The invention relates to a formulation of a male contraceptive comprising a progestin as well as methods of male contraception utilising progestins. Moreover, the invention relates to formulation further comprising an androgen as well as to methods using formulations comprising a progestin and an androgen so as to suppress spermatogenesis.

GENERAL BACKGROUND

Contraceptive methods for men are considered an essential component of world-wide reproductive health (Nieschlag and Behre; *Testosterone: action, deficiency, substitution*, 1998, Springer, Berlin, p 514). Hormonal methods of male contraception offer the advantages of high-reversibility and efficacy. In hormonal male contraception, the suppression of spermatogenesis is sought through the suppression of the gonadotropins leuteinizing hormone (LH) and follicle stimulating hormone (FSH) to undetectable levels within the endocrine feedback mechanism operating between the pituitary gland and the hypothalamus. Disadvantageously, suppression of these gonadotropins also induces symptoms related to androgen deficiency (Nieschlag and Behre; 1998, pp 513–528).

Male contraceptive methods seek to suppress FSH and LH, resulting in a depletion of intratesticular testosterone and cessation of spermatogenesis, whilst substituting peripheral testosterone with another androgen. This androgen has typically been testosterone itself and serves the endocrine androgenic role of testosterone such as to maintain libido, male sex characteristics, protein anabolism, hematopoesis and others. In short, the objective is to deplete the testes of testosterone whilst maintaining levels in the general circulation.

The suppression of spermatogenesis by administration of testosterones alone have been ineffective in inducing azoospermia. The administration of gonadotropin releasing hormone antagonists (GnRH antagonists) has circumvented part of the problem with the administration of high levels of testosterone alone but GnRH antagonists are unattractive for clinical use in their current preparations and are generally expensive to prepare.

The use of either the progestins cyproterone acetate or levonorgestrel were either ineffective in the suppression of spermatogenesis or, in higher doses, led to significant decreases in red blood cell count (Merrigiola et al, 1998; Merrigiola et al, 1997; Merrigiola et al, 1996; Bebb et al, 1996).

The use of a mixture of two compounds, one an androgen and another an estrogen, in combination is disclosed in U.S. Pat. No. 4,210,644.

A method towards the inhibition of spermatogenesis in men by administering testosterone percutaneously or orally and the progestin norethisterone acetate orally has been disclosed (Guerin and Rollet, 1988). However, high doses relative to amounts required by the present invention of each component were required to achieve azoospermia.

Thus, effective and efficient methods of male contraceptive by use of a male contraceptive formulation are not currently available.

BRIEF DESCRIPTION OF THE INVENTION

The invention disclosed herein solves this problem by providing in a first aspect, a male contraceptive formulation comprising an effective amount of a progestin, wherein said progestin possesses both androgenic and estrogenic properties. Most preferably, the formulation comprises the progestin norethisterone enanthate. Furthermore, the formulation may comprise norethisterone (NET), or derivatives thereof, and an androgen. Most preferably, in formulations comprising NET, or derivatives thereof and an androgen, the androgen is testosterone undecanoate.

A second aspect of the invention relates to the use of NET, or derivatives thereof, for the preparation of a pharmaceutical composition for use as a male contraceptive. Particularly, the use of NET enanthate or NET acetate for the preparation of a pharmaceutical composition for use as a male contraceptive is defined herein.

Similarly, the use of a combination of NET, or derivatives thereof, and an androgen for the preparation of a pharmaceutical composition for use as a male contraceptive is defined herein. Furthermore, the use of a combination of NET enanthate or NET acetate and testosterone undecanoate for the preparation of a pharmaceutical composition for use as a male contraceptive.

The use of a combination of NET esters and testosterone, or derivatives thereof, for the preparation of a male contraceptive formulation is also defined herein.

A third aspect of the invention relates to a method of providing male contraception comprising administering to an individual NET or a derivative thereof in an amount sufficient to suppress spermatogenesis.

DETAILED DESCRIPTION OF THE INVENTION

In the present application, a number of terms are used which are commonly used in the pharmaceutical field. An explanation of some of the special terms and concepts relevant to the present is given in the following items:

Estrogenic
  The term estrogenic when used alone or when applied to the term properties is intended to imply the characteristics of compounds exhibiting estrogen-like activities as defined by in vitro receptor-binding assays, transactivation assays, or in vivo assays as described in Example 2.

Androgenic
  The term androgenic when used alone or when applied to the term properties is intended to imply the characteristics of compounds exhibiting androgen-like activities as defined by in vitro antiproliferation assays, transfection assays, or in vivo assays as described in Example 3.

Spermatogenesis
  The term spermatogenesis is intended to mean the overall process of gametogenesis in the male. Spermatogenesis takes place in the seminiferous tubule and is directly regulated by levels of follicle stimulating hormone and androgen at the periphery of the seminiferous tubule, particularly upon the Sertoli cells.

Azoospermia

The term azoospermia represents a sperm content in semen sample below 1 million per mL (mill/mL) approaching levels of zero sperm content and are the result of suppression of spermatogenesis Oligozoospermia The term oligozoospermia represents a sperm content in semen between 20 and one million per mL (mill/mL) and are the result of inhibited levels of spermatogenesis.

Pearl-Index

The term Pearl Index is intended to indicate the number of pregnancies per 1200 months.

NET Derivatives

The term derivatives when applied to the term NET is intended to mean derivatives of 19-norethisterone, known under a variety of names including 17-Hydroxy-19-norpreg-4-en-20-yn-3-one. NET derivatives are intended to mean any modification of the 17-hydroxyl group without changing the oxidation state of carbon 17 of the compound as depicted in formula A. Thus, R can be selected from any number of chemical groups. These include groups so as to form ether, carboxylic ester, silyl, phosphate, sulphonate and sulfate.

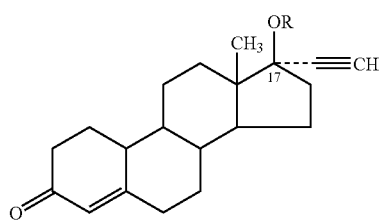

A

The term ether is intended to indicate that R is selected from the group comprising of optionally substituted $C_{1-18}$-alkyl, $C_{2-18}$-alkenyl, $C_{2-18}$-alkynyl, $C_{3-8}$-cycloalkyl, heterocyclyl, and aryl. In the present context the term "$C_{1-18}$-alkyl" used alone or as part of another group designates a linear or branched saturated hydrocarbon group having from one to eighteen carbon atoms, such as methyl, ethyl, n-propyl, isopropyl, cyclopropyl, n-butyl, isobutyl, sec-butyl, tert-butyl, cylcobutyl, pentyl, isopentyl, neopentyl, cyclopentyl, hexyl, cyclohexyl, pivalyl, undecanyl, dodecanyl, myristyl (tetradecanyl), palmityl (hexadecanyl) and stearyl (octadecanyl). In the present context the term "$C_{2-18}$-alkenyl" is intended to mean a linear or branched hydrocarbon group having from two to eighteen carbon atoms and containing one or more double bonds. Examples of $C_{2-18}$-alkenyl groups include olefins such as allyl, homo-allyl, vinyl, crotyl, butenyl, pentenyl, hexenyl, heptenyl and octenyl. Examples of $C_{2-8}$-alkenyl groups with more than one double bond include butadienyl, pentadienyl, hexadienyl, heptadienyl, hexatrienyl, heptatrienyl and octatrienyl groups as well as branched forms of these. In the present context the term "$C_{2-18}$-alkynyl" is intended to mean linear or branched hydrocarbon groups containing from two to eighteen carbon atoms and containing one or more triple bonds. Examples of $C_{2-18}$-alkynyl groups include acetylene, propynyl, butynyl, pentynyl, hexynyl, heptynyl and octynyl groups as well as branched forms of these. In the present context the term "$C_{3-8}$-cycloalkyl" is intended to cover three-, four-, five-, six- seven-, and eight-membered rings comprising carbon atoms only whereas the term "heterocyclyl" is intended to mean three-, four-, five-, six- seven-, and eight-membered rings wherein carbon atoms together with from 1 to 3 heteroatoms constitute said ring. The heteroatoms are independently selected from oxygen, sulphur, and nitrogen. Such $C_{3-8}$-cycloalkyl and term heterocyclyl rings may contain no unsaturated bonds or may contain one or more unsaturated bonds, however, if present, situated in such a way that an aromatic π-electron system does not arise.

Examples of "$C_{3-8}$-cycloalkyls" are cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Examples of "heterocyclyls" are 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro4H-thiazine, 4H-1,4-thiazine, tetrahydro-1,4-thiazine, 2H-1,2-oxazine, 4H-1,2-oxazine, 6H-1,2-oxazine, 2H1,3-oxazine, 4H-1,3-oxazine, 4H-1,4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane. 1,2,4-trioxolane, 1,2,3-triazoline and 1,2,3-triazolidine.

The term "aryl" is intended to comprise heteroaryl and fused aryl systems. When used in themselves or when described as substituted or optionally substituted are intended to mean the class of cyclic compounds in which themselves or moieties thereof possess chemical aromaticity. Aryls comprise of radicals of optionally mono-, di-, tri-, or tetra-substituted phenyl. In the present context the term "aryl" used alone or as part of another group is intended to mean an aromatic system. The term "heteroaryl" is intended to mean an aryl group where one or more carbon atoms have been replaced with heteroatoms such as nitrogen, sulphur, and/or oxygen atoms. These include a monoradical selected from the group comprising an optionally substituted, such as mono-, di-, tri-, or tetra-substituted furanyl, thiophenyl, pyrrolyl, phenoxazonyl, oxazolyl, thiazolyl, isothiazolyl, imidazolyl, pyrazolyl, isoxazolyl, imidazolyl isothiazolyl, oxadiazolyl, furazanyl, triazolyl, thiadiazolyl, piperidinyl, pyridinyl, pyridazinyl, pyrimidinyl, pyrazinyl, pyrazolyl and triazinyl. "Fused aryls" generally comprise fused ring systems between at least two aryls, at least one aryl fused with at least one heteroaryl, two heteroaryls, at least one aryl fused with a $C_{3-8}$-cycloalkyl, at least one aryl fused with a heterocyclyl, at least one heteroaryl fused with a heterocyclyl or at least one heteroaryl fused with a $C_{3-8}$-cycloalkyl. Fused ring systems, be it between aromatic systems, or between an aromatic system and a non-aromatic ring system are intended to mean where at least two rings share at least one chemical bond. Examples of fused aryls comprise naphthalenyl, phenanthrenyl, anthracenyl, acenaphthylenyl, fluorenyl, indenyl, indolyl, isoindolyl, indolinyl, benzofuranyl, benzothiophenyl, benzopyrazolyl, indazolyl, benzimidazolyl, benzthiazolyl, purinyl, quinolizinyl, quinolinyl, isoquinolinyl, cinnolinyl, coumaranyl, coumarinyl, phthalazinyl, quinazolinyl, quinoxalinyl, naphthyridinyl, pteridinyl, chromanyl, isochromanyl, thienofuranyl, carbazolyl, acridinyl, phenazinyl, phenothiazinyl, phenoxazinyl, thianthrenyl and azulenyl.

The term carboxylic ester when applied to NET is intended to mean the carboxylic acid derivatives of NET wherein R is the monoradical —C(=O)—R'. R' can be optionally substituted $C_{1-18}$-alkyl, $C_{2-8}$-alkenyl, $C_{2-18}$-alkynyl, $C_{3-8}$-cycloalkyl, heterocyclyl, and aryl as defined supra. Specific examples of carboxylic acid derivatives of NET are wherein the carboxylic acid or derivative of carboxylic acid used in the condensation to NET are selected from optionally substituted acetic acid, propionic acid, butanoic acid, pentanoic acid, hexanoic acid, heptanoic acid, octanoic acid (to give the enanthate), undecanoic acid, benzoic acid, toluic acid, salicylic acid, 3-(cyclopentyl)-propionic acid (to give the cypionate), cyclohexanecarboxylic acid, and 4-(butyl)-cyclohexanecarboxylic acid (to give the buciclate), pivalic acid, lauric acid, myristic acid, palmitic acid, stearic acid, acrylic acid, oleic acid and nicotinic acid.

The terms silyl, sulphonate and sulfate are intended to indicate that R is the radicals of —SiR'R"R''', —SO—R', —$SO_2$—R', respectively, wherein R', R" and R''' are independently selected from the group $C_{1-18}$-alkyl, $C_{2-8}$-alkenyl, $C_{2-18}$-alkynyl, $C_{3-8}$-cycloalkyl, heterocyclyl, and aryl as defined supra. The term phosphate is intended to mean indicate that R is the radicals of —P(O)(OR')(OR")(OR'''), wherein R', R" and R''' are independently selected from the group $C_{1-8}$-alkyl, $C_{2-18}$-alkenyl, $C_{2-18}$-alkynyl, $C_{3-8}$-cycloalkyl, heterocyclyl, and aryl as defined supra or hydrogen.

Progestin

The term progestin is synonymous with the term progestagen, and comprises a class of hormones naturally present in the body as well as synthetic and semi-synthetic derivatives thereof.

A unique approach of the contraceptive formulation disclosed herein is that of an effective amount of a single progestin possessing both androgenic and estrogenic properties.

In a male contraceptive formulation, the use of a compound with strong androgenic activity suppresses testicular spermatogenesis, and minimises the potential of side effects associated with androgen deficiency whilst feedback regulating LH and FSH from the hypothalamus and pituitary gland. The known estrogenic effect to suppress gonadotropin secretion results in a surprisingly fast and profound suppression of LH and FSH. It has surprisingly been found that the use of a single compound with estrogenic and androgenic properties is an effective means of suppressing spermatogenesis. A formulation comprising a single compound possessing estrogenic and androgenic properties has been found to be effective in male contraception The formulation defined by the invention has both estrogenic and androgenic effects. The progestin norethisterone (NET) possesses both these properties and is therefore a particularly preferred choice of progestin. Equally, norethisterone derivatives are suitable to fulfil the dual role of the progestin. In particular, carboxylic esters of the 17-hydroxy group are especially preferred embodiments of the invention. Norethisterone acetate (NET-A) and norethisterone enanthate (NET-EN) are considered to be particularly attractive embodiments.

In a particularly interesting embodiment, the formulation further comprises an androgen. Testosterone or testosterone derivatives are preferred such androgens. Most preferably, testosterone esters are selected as androgens. As is known to the person skilled in the art, a whole host of testosterone esters are effective androgens and may be selected form the group comprising testosterone propionate, testosterone undecanoate, testosterone enanthate, testosterone cypionate and testosterone buciclate. In a particularly preferred embodiment, the androgen is testosterone undecanoate.

It is preferred that in the formulations comprising a progestin and an androgen, the progestin be selected from NET or its derivatives, such as its carboxylic esters. Particularly, it is preferred that in these instances, the progestin be NET enanthate or NET acetate, most particularly NET enanthate. One such preferred formulation comprises testosterone undecanoate and norethisterone enanthate.

The use of a compound, such as a NET derivative, having strong androgenic properties and estrogenic properties is advantageous in that this strong androgenic activity minimises the potential of side effects related to androgen deficiency. The estrogenic activity of NET, on the other hand, suppresses gonadotropin secretion. A formulation comprising a progestin and androgen effectively and rapidly suppresses spermatogenesis in trial studies. Without being limited to a particularly mechanism, it is theorised that the rapidity of the suppression, in comparison to trials using progestins which are not strongly androgenic and estrogenic but instead are anti-androgenic or only weakly androgenic, is not solely due to the anti-gonadotropin activity of NET, but also due to an additional direct and strong effect on the testes. This direct testicular effect is likely to be mediated through the androgenic and estrogenic activity of NET.

Doses

Preferably, the formulation comprises a dose of NET or of the NET derivative corresponding to a daily release of the NET derivative ranging between 1 and 10 mg, such as 1, 2, 3, 4, 5, 6, 7, 8, 9, or 10 mg.

Correspondingly, the dose of the NET derivative should range between 100 and 500 mg for each 6-week administration, particularly between 200 and 400 mg for each 6-week administration or about 200 mg for each 6-week administration.

The levels of progestin, such as NET or its derivatives, are to be sufficient to suppress spermatogenesis. In general, the levels of progestin are to be sufficient to induce oligozoospermia or azoospermia. In men whose sperm has a less than normal fertilising capacity, either as a result of the contraceptive method, other treatments or naturally, complete azoospermia may not be required for effective contraception. In such cases, levels of progestin such as NET need merely be sufficient to induce oligozoospermia.

Accordingly, the formulation may comprise progestin in sufficient amounts to lower the sperm concentration to not more than 3 million/mL of semen, such as not more than 2 million/mL, 1 million/mL, 0.5 million/mL, 0.25 million/mL, or 0,1 million/mL. It is preferred however that the progestin be in sufficient amounts so as to lower the sperm concentration to not more than 0.1 million/mL.

Furthermore, the levels of progestin in the formulation may be such that upon following a method disclosed herein, the Pearl-index is not more than 1.4, such as not more than 1.2, 1.0. 0.8, 0.7. 0.6, 0.5, 0.4, 0.3, 0.2, or not more than 0.1.

The effective levels of progestin in the circulation should preferably be sustained for not less than 1 week. The formulation and/or consequent method of administration are preferably designed so as to maintain effective levels of progestin in the system for as long as desired by the man, such as for not less than 2, 3, 4, 5, 6, 7, 8, 9, 10, 11, or 12 weeks.

As stated earlier in relation the embodiments of the formulation not further comprising an androgen, the formulation comprising a combination of NET or derivatives thereof and the androgen must also be in sufficient amounts to suppress spermatogenesis.

Preferably, the formulation comprising NET and an androgen comprises a dose of NET or of the NET derivative corresponding to a daily release of the NET derivative ranging between 1 and 10 mg, such as 1, 2, 3, 4, 5, 6, 7, 8, 9, or 10 mg. Correspondingly, the dose of the NET derivative should range between 100 and 500 mg for each 6-week administration, particularly between 200 and 400 mg for each 6-week administration or about 200 mg for each 6-week administration.

In formulations comprising the progestin and an androgen, the dose of the latter should correspond to a daily release of the testosterone derivative corresponding to a daily release of testosterone in amounts ranging between 5 and 35 mg, such as preferably corresponding to a daily dose of testosterone ranging between 15 and 30 mg.

In such embodiments comprising an androgen and wherein the androgen is testosterone undecanoate, a dose of testosterone undecanoate ranging between 800 and 1500 mg for each 6-week administration is anticipated, such as a dose of about 1000 mg for each 6-week administration.

In formulations comprising the progestin and an androgen, wherein the progestin is NET enanthate or NET acetate, the dose of the latter should correspond to a daily release of the NET ester ranging between 1 and 10 mg. Moreover, the dose of the NET derivative preferably ranges between 100 and 500 mg for each 6 week administration, such as between 150 and 250 mg for each 6 week administration such as corresponding to dose of NET acetate of about 200 mg for each 6 week administration. In this same formulation, the dose of the androgen may correspond to a daily release of the testosterone derivative corresponding to a daily release of testosterone in amounts ranging between 5 and 35 mg, such as preferably corresponding to a daily dose of testosterone ranging between 15 and 30 mg. Accordingly, the dose of the testosterone derivative may correspond to a dose of testosterone between 500 and 1200 mg for each 6-week administration, such as corresponding to a dose of testosterone of about 1000, 800, or 650 mg for each 6-week administration. Preferably, the androgen is testosterone undecanoate.

The formulation comprising NET or derivatives thereof and the androgen should preferably be in sufficient amounts to lower the sperm concentration to not more than 3 million/mL, most preferably to sperm concentrations of not more than 0.1 million/mL.

It is an objective of the invention to provide a formulation comprising NET or derivatives thereof and the androgen in sufficient amounts such that Pearl-index is lowered to not more than 1.4, such as not more than 1.2, 1.0. 0.8, 0.7. 0.6, 0.5, 0.4, 0.3, 0.2, or not more than 0.1.

Moreover, a further objective of the invention is to provide a formulation wherein effective circulating levels of the combination of progestin and androgen are sustained for not less than 1 week. Preferably, the formulation and consequent method of administration are such that effective circulating levels of the combination of progestin and androgen are sustained for not less than 2 weeks, such as not less than 4 weeks, 6 weeks, 8 weeks, 10 weeks or 12 weeks.

Methods of Administration

The method of administration should preferably be by non-oral means such as by intramuscular injection, subcutaneous implant, transdermal patch or percutaneous application. Thus, the formulation may be adapted to be administered via intramuscular injection, intravenous injection, subcutaneous implantation, subcutaneous injection or transdermal preparation.

Intramuscular injections of NET derivatives has led to surprisingly effective serum levels with regards to suppression of spermatogenesis. Given the pharmacodynamics of NET derivatives, this method of administration is considered a particularly attractive embodiment towards achieving effective amounts of the progestin in the blood stream. Moreover, by circumventing the hepatic first pass, lower doses are required to achieve effective amounts.

However, given that the method of administration is a means to an end, that is to say a method of delivering the progestin in the formulation in any of its embodiments at an effective level, other methods of administration are anticipated. The pharmaceutical formulation may be administered parenterally by injection, infusion or implantation (intravenous, intramuscular, intraarticular, subcutaneous or the like) in dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in the textbook entitled "Remington's Pharmaceutical Sciences".

Compositions for parenteral use may be presented in unit dosage forms, e.g. in ampoules, or in vials containing several doses and in which a suitable preservative may be added. The composition may be in form of a solution, a suspension, an emulsion, an infusion device or a delivery device for implantation or it may be presented as a dry powder to be reconstituted with water or another suitable vehicle before use. One or more covehicles, such as ethanol, may also be employed. Apart from the active drug substance, the compositions may comprise suitable parenterally acceptable carriers and/or excipients or the active drug substance may be incorporated into microspheres, microcapsules, nanoparticles, liposomes or the like for controlled release. Furthermore, the composition may, in addition, conveniently comprise suspending, solubilising, stabilising, pH-adjusting agents and/or dispersing agents.

As indicated above, the pharmaceutical compositions according to the invention may comprise the active drug substances in the form of a sterile injection. To prepare such a composition, the suitable active drug substances are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. In cases where the progestin, the androgen, or both are only sparingly or slightly soluble in water, a dissolution enhancing or solubilising agent can be added or the solvent may apart from water comprise 10–60% w/w of propylene glycol or the like.

As mentioned, controlled release parenteral compositions may be in form of aqueous suspensions, microspheres, microcapsules, magnetic microspheres, oil solutions, oil suspensions, emulsions or the active drug substance may be incorporated in biocompatible carrier(s), liposomes, nanoparticles, implants or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and poly(lactic acid).

Biocompatible carriers which may be used when formulating a controlled release parenteral formulation are, e.g., carbohydrates such as dextrans, proteins such as albumin, lipoproteins or antibodies.

Materials for use in implants are, e.g., non-biodegradable as, e.g., polydimethylsiloxane, or biodegradable such as, e.g., poly(caprolactone), poly(lactic acid), poly(glycolic acid) or poly(ortho esters).

A plethora of transdermal patches suitable as delivery systems may be selected from the types described or alluded to in 'Transdermal Drug Delivery; Developmental Issues and Research Initiatives' (Hadgraft and Guy, Marcel Dekker Inc., 1989), by transdermal patches of the type disclosed in U.S. Pat. Nos. 4,743,249, 4,906,169, 5,198,223, 4,816,540, or 5,422,119 or by the transdermal delivery process disclosed in U.S. Pat. No. 5,023,084 or by any transdermal patch known to the person skilled in the art. Moreover, absorption enhancers or skin permeation enhancers of the type disclosed in U.S. Pat. Nos. 4,379,454 or 4,973,468 or using any such enhancers known to the person skilled in the art. Transscrotal patches are attractive embodiments of the method of administration. Transdermal therapeutic systems, containing the progestin, the androgen, or both components may be based on iontophoresis, diffusion, or a combination of these two effects.

Delivery systems wherein the formulation is administered topically on the skin for percutaneous absorption in dosage forms or formulations containing conventionally non-toxic pharmaceutical acceptable carriers and excipients including microspheres and liposomes. Although transdermal patches are one of the preferred methods of percutaneous absorption, it is anticipated that the formulations may be adapted to be suitable for use as creams, ointments, lotions, liniments, gels, hydrogels, solutions, suspensions, sticks, sprays, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes and skin protective agents.

Examples of emulsifying agents are naturally occurring gums, e.g. gum acacia or gum tragacanth, naturally occurring phosphatides, e.g. soybean lecithin and sorbitan monooleate derivatives.

Examples of antioxidants are butylated hydroxy anisole (BHA), ascorbic acid and derivatives thereof, tocopherol and derivatives thereof, butylated hydroxy anisole and cysteine.

Examples of preservatives are parabens, such as methyl or propyl p-hydroxybenzoate and benzalkonium chloride.

Examples of humectants are glycerin, propylene glycol, sorbitol and urea.

Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, Transcutol®, and Azone®.

Examples of chelating agents are sodium EDTA, citric acid and phosphoric acid.

Examples of gel forming agents are Carbopol, cellulose derivatives, bentonite, alginates, gelatin and polyvinylpyrrolidone.

Subcutaneous implants are well known to the person skilled in the art and a plurality of such implants are suitable methods of administration. Subcutaneous implantation methods are preferably non-irritating and mechanically resilient. The implants may be of matrix type, of reservoir type or hybrids thereof. In matrix type devices, the carrier material may be porous or non-porous, solid or semi-solid, and permeable or impermeable to the active compound or compounds. The carrier material may be biodegradable or may slowly erode after administration. In some instances, the matrix is non-degradable but instead relies on the diffusion of the active compound through the matrix for the carrier material to degrade. An alternative subcutaneous implant methods utilises reservoirs devices wherein the active compound or compounds are surrounded by a rate controlling membrane, ideally a membrane independent of component concentration (possessing zero-order kinetics). Devices consisting of a matrix surrounded by a rate controlling membrane are hybrids also anticipated as a method of administration and may optionally be mechanically operated.

Both reservoir and matrix type devices may comprise of materials such as polydimethylsiloxane, such as Silastic™, or other silicone rubbers. Matrix materials may be insoluble polypropylene, polyethylene, polyvinyl chloride, ethylvinyl acetate, polystyrene and polymethacrylate, as well as glycerol esters of the glycerol palmitostearate, glycerol stearate and glycerol behenate type. Materials may be hydrophobic or hydrophilic polymers and optionally comprise of solubilising agents.

In general, subcutaneous implant devices may be slow-release capsules made with any suitable polymer, as described in U.S. Pat. Nos. 5,035,891 and 4,210,644, conferring such properties are anticipated and may be of the sort known to the person skilled in the art.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition may be obtained by using a suitable mixture of the above-mentioned approaches.

In a membrane-moderated system, the active drug substance is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active drug substance is only permitted to be released through the ratecontrolling polymeric membrane. In the drug reservoir, the active drug substance may either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active drug substance is formed by directly dispersing the active drug substance in an adhesive polymer and then—by, e.g., solvent casting—spreading the adhesive containing the active drug substance onto a flat sheet of substantially drug-impermeable metallic plastic backing to form a thin drug reservoir layer.

A matrix dispersion-type system is characterized in that a reservoir of the active drug substance is formed by substantially homogeneously dispersing the active drug substance in a hydrophilic or lipophilic polymer matrix and then, the drug-containing polymer is molded into disc with a substantially well-defined surface area and controlled thickness. The adhesive polymer is spread along the circumference to form a strip of adhesive around the disc.

A microreservoir system may be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

In embodiments wherein the formulation comprises progestin, non-limiting examples of methods of administration are outlined above. Moreover, it is anticipated that in embodiments wherein an androgen is further administered, that is to say a combination of two active component substances, it is anticipated that each component may be in separate vials or vesicles or the like. For example, the components may use non-identical vehicles, solvents, buffers, parenterally acceptable carriers and/or excipients or the active drug substance may independently be incorporated into microspheres, microcapsules, nanoparticles, liposomes or the like for differential controlled release. Furthermore, the compositions may, in addition, conveniently comprise non-identical suspending, solubilising, stabilising, pH-adjusting agents and/or dispersing agents. The non-identical compositions comprise a formulation in one package.

In one embodiment of the invention, the formulation comprising both progestin and androgen is administered by non-oral means, such as methods of administrations selected from the group consisting of intramuscular injection, intravenous injection, subcutaneous implantation, subcutaneous injection and transdermal preparations.

In an alternative adaptation of the formulation, the methods of administrations of the progestin are selected form the group consisting of intramuscular injection, intravenous injection, subcutaneous implantation, subcutaneous injection and transdermal preparations and the methods of administrations of the androgen are selected from the group consisting of oral administration, intramuscular injection, intravenous injection, subcutaneous implantation, subcutaneous injection and transdermal preparations. That is to say that each active component in the formulation is administered in two separate dosage forms, in two non-identical compositions and/or by two different methods of administration.

The preferred methods of administration are those wherein both compounds are administered by a method selected from the group comprising subcutaneous implant, intramuscular injection and transdermal patch.

A further aspect of the invention relates to the use of NET, or derivatives thereof, for the preparation of a pharmaceutical composition for use as a male contraceptive. Preferably, the NET derivative is a carboxylic ester, particularly NET enanthate or NET acetate, preferably NET enanthate.

Moreover, the invention encompasses to the use of a combination of NET or derivatives thereof and an androgen for the preparation of a male contraceptive formulation. Thus, the use of a combination of NET, or derivatives thereof, and an androgen for the preparation of a preparation of a pharmaceutical composition for use a male contraceptive is defined by the present invention. In particular, one embodiment of the invention encompasses the use of a combination of NET esters and testosterone, or derivatives thereof, for the preparation of a pharmaceutical composition for use as a male contraceptive. Preferably, the NET derivative is a carboxylic ester, particularly NET enanthate or NET acetate, preferably NET enanthate. Preferably, the testosterone derivative used is a testosterone ester, particularly testosterone propionate, testosterone undecanoate, testosterone decanoate, testosterone enanthate, testosterone cypionate and testosterone buciclate, preferably testosterone undecanoate.

It is most preferred that NET enanthate and testosterone undecanoate are used for the preparation of a pharmaceutical composition for use as male contraceptive.

The invention further encompasses a method of providing male contraception comprising administering to an individual NET or a derivative thereof in an amount sufficient to suppress spermatogenesis such as by administering a non-oral formulation as described supra.

Furthermore, it is preferred that a method of providing male contraception comprises administering to an individual a combination of NET or a derivative thereof and an androgen as a non-oral formulation in an amount sufficient to suppress spermatogenesis.

It is preferred that in such a method, the androgen is testosterone or a derivative thereof, such as a testosterone ester, particularly testosterone undecanoate.

A preferred embodiment of the method of providing male contraception comprises administering to an individual a combination of NET enanthate and testosterone undecanoate as a non-oral formulation in an amount sufficient to suppress spermatogenesis, particularly by means of a transdermal patch, intramuscular injection or by a subcutaneous implant.

The present invention is further described in the following examples which are not in any way intended to limit the scope of the invention as claimed.

EXAMPLES

Example 1

Clinical Study Design

In this study design (Table 1), the three groups A, B and C follow separate regimens. To Group A is administered 200 mg of NET enanthate intramuscularly every six weeks starting day 0 and testosterone undecanoate intramuscularly (1000 mg) on weeks 2 and six and every following six weeks. This regimen is followed until week 18. To group B is administered 400 mg of NET enanthate intramuscularly and testosterone undecanoate intramuscularly (1000 mg) every six weeks starting day 0. This regimen was followed until week 18. Group C is administered 10 mg of NET acetate daily p.o and 1000 mg of testosterone undecanoate intramuscularly every six weeks for 18 weeks.

Examinations and analyses are performed on group members throughout the administration period to establish the relative and absolute efficacy of each of the regimens. Moreover, examinations and analyses are performed until week 56.

In studies combining NET and an androgen, the use of TU in trials of male contraception offers considerable advantages compared to other testosterone esters because of its favourable injection interval of 6 weeks. However, the use of other testosterone esters in comparable doses with other injection intervals or by other means of administration offer comparable contraceptive means when used in combination with NET esters. The basis for the advantages of the present invention resides in the use of NET esters, alone or in combination with an androgen, preferably by intramuscular or oral administration.

Hartung, *In Vitro and In Vivo Models to Characterise Estrogens and Antiestrogens;* Springer-Verlag, Berlin, Heidelberg, 1999.

The basic principle behind receptor binding assays lies in that the binding of substances to the estrogen receptor is a pre-requisite for the compound to exhibit estrogen-like activity. Binding affinities or dissociation constants are used as measures of the substance to bind to the estrogen receptor.

Transactivation assays for the detection of estrogenic activity are based on the ability of the estrogen receptor to cause gene activation in a ligand-dependant way. The binding of an estrogenic substance results in ligand-activated formation of a receptor dimer which then binds to a specific nucleotide sequence in the promoter segment of a target gene.

TABLE 1

1.1.1 Study flow chart

| | Screening | | Start | | | Treatment | | | | | | | | Observation | | | |
|---|---|---|---|---|---|---|---|---|---|---|---|---|---|---|---|---|---|
| Visit | 1 | 2 | 3 | 4 | 5 | 6 | 7 | 8 | 9 | 10 | 11 | 12 | 13 | 14 | 15 | 16 |
| Assessment | A | B[1] | day 0[2] | W2[3] | W4 | W6 | W8 | W12 | W16 | W18 | W20 | W24 | W28 | W38 | W44 | W56 |
| Group A | | | | | | | | | | | | | | | | | |
| NET-EN administration (mg) | | | 200 | | | 200 | | 200 | | 250 | | | | | | | |
| TU administration (mg) | | | | | 1000 | 1000 | | 1000 | | 1000 | | | | | | | |
| Group B | | | | | | | | | | | | | | | | | |
| NET-EN administration (mg) | | | 400 | | | 400 | | 400 | | 400 | | | | | | | |
| TU administration (mg) | | | | | 1000 | 1000 | | 1000 | | 1000 | | | | | | | |
| Group C | | | | | | | | | | | | | | | | | |
| NET-A administration (mg) | | | 10 mg daily p.o. V102 | | | | | V314 | | V5187 | | | | | | | |
| TU administration (mg) | | | 1000 | | | 1000 | | 1000 | | 1000 | | | | | | | |
| Informed Consent/Demographics | ABC | | | | | | | | | | | | | | | | |
| Check of Inclusion/Exclusion | ABC | | ABC | | | | | | | | | | | | | | |
| Randomization/Diary dispensed | | | ABC | | | | | | | | | | | | | | |
| Medical/androl./medication history | ABC | ABC | ABC | | | | | | | | | | | | | | |
| Vital signs | ABC | ABC | | | ABC | | ABC | ABC | ABC | | ABC | ABC | ABC | ABC | ABC | ABC | |
| Physical examination | ABC | | | | ABC | | ABC | ABC | ABC | | ABC | ABC | ABC | ABC | ABC | ABC | |
| Andrological examination | ABC | | | | ABC | | ABC | ABC | ABC | | ABC | ABC | ABC | ABC | ABC | ABC | |
| Semen analysis | ABC | ABC | | | ABC | | ABC | ABC | ABC | | ABC | ABC | ABC | ABC | ABC | ABC | |
| General laboratory | ABC | | | | | | | ABC | | | | ABC | | ABC | | ABC | |
| Hormones | ABC | ABC | | A | ABC | ABC | ABC | ABC | ABC | ABC | ABC | ABC | ABC | ABC | ABC | ABC | |
| Exam./Ultrasonography of prostate | | ABC | | | | | | ABC | | | | ABC | | ABC | | ABC | |
| Ultrasonography of testes | | ABC | | | | | | ABC | | | | ABC | | ABC | | ABC | |
| Return of diary/vials, if available | | | | | C | C | C | C | C | C | C | C | C | | | | |
| AEs/concomitant medication | | | | A | ABC | ABC | ABC | ABC | ABC | ABC | ABC | ABC | ABC | ABC | ABC | ABC | |
| Questionnaire | ABC | ABC | | | ABC | | ABC | ABC | ABC | | ABC | ABC | ABC | ABC | ABC | ABC | |

[1]At least 7 days after visit 1
[2]Not more than 8 weeks after visit 1
[3]A deviation of ± 5 days will be tolerated Example 2

Estrogenic Properties

Receptor binding assays, tranactivation assays, and in vivo assays for establishing estrogenic activity are described in *Handbook of experimental Pharmacology, Vol. 135/II, Estrogens and Antiestrogens II, Pharmacology and Clinical Applications of Estrogens and Antiestrogens;* M. Ottel and E. Schillinger (editors); K.-H. Fritzemeier and C. Hegele- A number a of test systems and method for the in vivo characterisation of estrogenic activity. The Allen-Doisy Assay is one such assay in which the vaginal cytology of ovariectomised rodents is examined. Given estrogenic compounds induce proliferation and keratinisation of the vaginal epithelium, the microscopic examination of vaginal smears of ovariectomised rodents for evaluation of epithelial thickness and cornification is a reliable indicator of estrogenic activity.

Other in vivo test systems to test estrogenicity in the vagina include determination of alterations in the vaginal epithelial mitotic index, of a reduction in vaginal tetrazolium, of the vaginal opening in immature rodents and of the vaginatrophic response as well as by the measurement of sialic acid production in ovariestomised female rodents.

Many assays consisting of determining the estrogenicity in the uterus of rodents and primates are known to the person skilled in the art.

Tests on the influence of estrogens on hypothalamic-pituitary-ovarian feedback typically comprises of determining the change in gonadal weight given the principle that the administration of gonadal steroids leads of reduced growth of the ovaries and testes. Alternatively, the reduction in the peak levels of the gonadotropins FSH/LH during the preovulatory phase in female rodents can be a measured.

Example 3

Androgenic Properties

Assays, both in vivo and in vitro, for establishing androgenic activity are described in *Androgens II and Anti-Androgens*, F. Neuman, F. Baher, J. Brotherton, K.-J. Gräf, S. H. Hasan, H. J. Horn, A. Hughes, G. W. Oertel, H. Steinbeck, H. E. Voss, R. K. Wagner, Springer-Verlag, Berlin, Heidelberg, 1974.

Receptor tests for androgenicity are analogous to estrogenicity tests and generally utilise rat prostrate cytosol for tests on androgen receptors. A transfection assay of the androgen receptor has been established by Fuhrmann, Bengston, Repenthin, and Schillinger (*J. Steroid Biochem. Mol. Biol.*, 1992, 42(8), 787). An antiproliferation test with the human prostate cancer cell line LCNaP, which expresses the androgen receptor and can be stimulated in growth by androgens has been developed. If a single administration of a test compound leads to growth stimulation, this can be explained by the androgenic activity of the compound.

REFERENCES

E. Nieschlag and H. M. Behre; *Testosterone in Male Contraception*. In E. Nieschlag and H. M. Behre, eds. *Testosterone: action, deficiency, substitution*, 1998, Springer, Berlin, pp 513–528.

M. C. Merrigiola, W. J. Bremner, A. Constantino, A. Pavani, M. Capelli and C. Flamigni; Low Dose of Cyproterone Acetate and Testosterone Enanthate for Contraception in Men., *Hum Reprod.*, (1998) 13, 1225–1229.

M. C. Merrigiola, W. J. Bremner, A. Constantino, A. Pavani, M. Capelli and C. Flamigni, An Oral Regimen of Cyproterone Acetate and Testosterone Undecanoate for Spermatogenic Suppression in Men, *Fertil. Steril.* (1997); 68, 84–850.

M. C. Merrigiola, W. J. Bremner, C. A. Paulsen, A. Valdiserri, L. Incorvaia, R. Motta, A. Pavani, M. Capelli and C. Flamigni, A Combined Regimen of Cyproterone Acetate and Testosterone Enanthate as a Potentially Highly effective Male Contraceptive, *J. Clin. Endocrinol.* (1996); 81, 3018–3023.

R. A. Bebb, B. D. Anawalt, R. B. Christensen, C. A. Paulsen, W. J. Bremner and A. M. Matsumoto., Combined Administration of Levonorgestrel and Testosterone Induces More Rapid and Effective Suppression of Spermatogenesis than Testosterone Alone: A Promising Contraceptive Approach., *J. Clin Endocriniol. Metab.*, (1996) 81, 757–762.

J. F. Guerin and J. Rollet, *International Journal of Andrology*, 1988, 11, pp.187–199.

Hadgraft and Guy; *Transdermal Drug Delivery; Developmental Issues and Research Initiatives*, Marcel Dekker Inc., 1989.

M. Ottel and E. Schillingeer (editors), *Handbook of Experimental Pharmacology*, Vol. 135/II, Androgens and Antiestrogens II, Pharmacology and Clinical Applications of Estrogens and Antiestrogens; K.-H. Fritzemeier and C. Hegele-Hartung, *In Vitro and In Vivo Models to Characterise Estrogens and Antiestrogens;* Springer-Verlag, Berlin, Heidelberg, 1999.

F. Neuman, F. Baher, J. Brotherton, K. -J. Gräf, S. H. Hasan, H. J. Horn, A. Hughes, G. W. Oertel, H. Steinbeck, H. E. Voss, R. K. Wagner, *Androgens II and Anti-Androgens*, Springer-Verlag, Berlin, Heidelberg, 1974.

Fuhrmann, Bengston, Repenthin, and Schillinger, *J. Steroid Biochem. Mol. Biol.*, 1992, 42(8), 787).

The invention claimed is:

1. A method of suppressing spermatogenesis, inducing azospermia and/or inducing oligospermia in a male, comprising: i) administering to the male an effective amount of a testosterone ester by intramuscular injection, subcutaneous implantation, or subcutaneous injection; and, ii) administering to the male an effective amount of a norethisterone modified at the 17-hydroxyl group to an ether, carboxylic ester, silyl, phosphate, sulfonate or sulfate, which possesses both androgenic and estrogenic properties.

2. The method of claim 1, wherein the testosterone ester and norethisterone are administered separately.

3. The method of claim 2, wherein the norethisterone is administered by intramuscular injection, intravenous injection, subcutaneous implantation, subcutaneous injection or transdermally.

4. The method according to claim 2, wherein the injection or implantation of the testosterone ester is in intervals of not less than 6 weeks.

5. The method according to claim 4, wherein the dose of testosterone ester provides a dose of testosterone ranging between 500 and 1200 mg for a 6-week administration.

6. The method according to claim 4, wherein the testosterone ester is testosterone undecanoate and the dose of testosterone undecanoate ranges between 800 and 1500 mg for a 6-week administration.

7. The method according to claim 4, wherein the testosterone ester is testosterone undecanoate and the dose of testosterone undecanoate is 1000 mg for a 6-week administration.

8. The method of claim 1, wherein the testosterone ester and norethisterone are administered together by intramuscular injection, subcutaneous implantation, or subcutaneous injection.

9. The method according to claim 8, wherein the injection or implantation of the testosterone ester and norethisterone is in intervals of not less than 6 weeks.

10. The method according to claim 8, wherein the injection or implantation of the testosterone ester and norethisterone is in intervals of not less than 8 weeks.

11. The method according to claim 8, wherein the injection or implantation of the testosterone ester and norethisterone is in intervals of not less than 10 weeks.

12. The method according to claim 8, wherein the dose of testosterone ester provides a dose of testosterone ranging between 500 and 1200 mg for a 6-week administration.

13. The method according to claim 8, wherein the testosterone ester is testosterone undecanoate and the dose of testosterone undecanoate ranges between 800 and 1500 mg for a 6-week administration.

14. The method according to claim 8, wherein the testosterone ester is testosterone undecanoate and the dose of testosterone undecanoate is 1000 mg for a 6-week administration.

15. The method according to claim 1, wherein the modified norethisterone is administered such that a daily release of a modified norethisterone in an amount between 1 and 10 mg is provided.

16. The method according to claim 1, wherein the modified norethisterone is a carboxylic ester of norethisterone.

17. The method according to claim 16, wherein the carboxylic ester of norethisterone is an acetate ester and/or an enanthate ester.

18. The method according to claim 16, wherein the carboxylic ester of norethisterone is norethisterone enanthate.

19. The method according to claim 1, wherein the amount of said modified norethisterone and said testosterone ester provides effective levels of said modified norethisterone and said testosterone ester in the circulation for not less than 6 weeks.

20. The method according to claim 19, wherein the dose of modified norethisterone is between 100 and 500 mg.

21. The method according to claim 19, wherein the dose of modified norethisterone is between 200 and 400 mg.

22. The method according to claim 19, wherein the effective levels in the circulation are sustained for not less than 10 weeks.

23. The method according to claim 1, wherein the testosterone ester is selected from the group consisting of testosterone propionate, testosterone undecanoate, testosterone enanthate, testosterone cypionate and testosterone buciclate.

24. The method according to claim 1, wherein the testosterone ester is testosterone undecanoate.

25. The method according to claim 1, wherein the testosterone ester is administered such that a daily release of testosterone in an amount ranging between 5 and 35 mg is provided.

26. The method according to claim 1, wherein the testosterone ester is administered such that a daily release of testosterone in an amount ranging between 15 and 30 mg is provided.

27. The method according to claim 24, wherein the dose of testosterone undecanoate provides a dose of testosterone ranging between 500 and 1200 mg for a 6-week administration.

28. The method according to claim 24, wherein the dose of testosterone undecanoate ranges between 800 and 1500 mg for a 6-week administration.

29. The method according to claim 24, wherein testosterone undecanoate is in a dose of 1000 mg for a 6-week administration.

30. The method according to claim 1, wherein said modified norethisterone and testosterone ester are both administered by intramuscular injection, or subcutaneous implant.

31. The method according to claim 1, wherein said modified norethisterone and testosterone ester are both administered by intramuscular injection.

32. The method of claim 2, wherein the testosterone ester is administered by intramuscular injection and the norethisterone is administered by transdermal patch.

33. The method according to claim 1, which is effective for male contraception.

* * * * *